United States Patent [19]

Leung et al.

[11] Patent Number: 5,575,997
[45] Date of Patent: Nov. 19, 1996

[54] BIOCOMPATIBLE MONOMER AND POLYMER COMPOSITIONS

[75] Inventors: Jeffrey C. Leung; Jeffrey G. Clark, both of Raleigh, N.C.

[73] Assignee: Tri-Point Medical Corporation, Raleigh, N.C.

[21] Appl. No.: 461,931

[22] Filed: Jun. 5, 1995

Related U.S. Application Data

[62] Division of Ser. No. 215,584, Mar. 22, 1994, Pat. No. 5,514,371, which is a division of Ser. No. 40,618, Mar. 31, 1993, Pat. No. 5,328,687.

[51] Int. Cl.$^6$ .................... A61K 31/785; A61K 31/795; A61K 9/14; A61F 2/28

[52] U.S. Cl. .................... 424/78.35; 424/426; 424/451; 424/489; 526/297; 526/300; 526/341; 514/963; 264/4.33

[58] Field of Search .................... 424/78.35, 426, 424/451, 489; 526/297, 300, 341; 514/963; 264/4.33

[56] References Cited

U.S. PATENT DOCUMENTS

| | | | |
|---|---|---|---|
| 2,721,858 | 10/1955 | Joyner et al. | 528/267 |
| 2,765,332 | 10/1956 | Coover, Jr. et al. | 558/307 |
| 3,223,083 | 12/1965 | Cobey | 606/92 |
| 3,254,111 | 5/1966 | Hawkins et al. | 558/381 |
| 3,527,841 | 9/1970 | Wicker, Jr. et al. | 528/354 |
| 3,554,990 | 1/1971 | Quinn et al. | 428/522 |
| 3,559,652 | 2/1971 | Banitt et al. | 606/214 |
| 3,564,078 | 2/1971 | Wicker, Jr. et al. | 424/78.06 |
| 3,591,676 | 7/1971 | Hawkins et al. | 424/78.06 |
| 3,667,472 | 6/1972 | Halpern | 606/214 |
| 3,722,599 | 3/1973 | Robertson et al. | 606/214 |
| 3,759,264 | 9/1973 | Nolan et al. | 606/214 |
| 3,909,408 | 9/1975 | Ishida et al. | 210/757 |
| 3,940,362 | 2/1976 | Overhults | 523/116 |
| 3,995,641 | 12/1976 | Kronenthal et al. | 606/214 |
| 4,127,382 | 11/1978 | Perry | 8/181 |
| 4,364,876 | 12/1982 | Kimura et al. | 558/443 |
| 4,524,093 | 6/1985 | Devry | 427/389 |
| 4,578,061 | 3/1986 | Lemelson | 604/164 |
| 4,582,648 | 4/1986 | Hirakawa | 558/442 |
| 4,675,173 | 6/1987 | Woods et al. | 430/540 |
| 4,744,364 | 5/1988 | Kensey | 604/15 |
| 4,804,691 | 2/1989 | English et al. | 523/118 |
| 4,832,688 | 5/1989 | Sagae et al. | 604/53 |
| 4,852,568 | 8/1989 | Kensey | 128/325 |
| 4,890,612 | 1/1990 | Kensey | 606/213 |
| 4,900,303 | 2/1990 | Lemelson | 604/54 |
| 5,021,059 | 6/1991 | Kensey et al. | 606/213 |
| 5,053,046 | 10/1991 | Janese | 606/215 |
| 5,061,274 | 10/1991 | Kensey | 606/213 |
| 5,108,421 | 4/1992 | Fowler | 606/213 |
| 5,112,652 | 5/1992 | Greene | 427/342 |
| 5,129,882 | 7/1992 | Weldon et al. | 604/96 |
| 5,192,300 | 3/1993 | Fowler | 606/213 |
| 5,192,309 | 3/1993 | Stupka et al. | 623/2 |
| 5,221,259 | 6/1993 | Weldon et al. | 604/96 |
| 5,222,974 | 6/1993 | Kensey et al. | 606/213 |
| 5,275,616 | 1/1994 | Fowler | 606/213 |
| 5,282,827 | 2/1994 | Kensey et al. | 606/215 |
| 5,292,332 | 3/1994 | Lee | 606/213 |
| 5,324,306 | 6/1994 | Makower et al. | 606/213 |
| 5,330,446 | 7/1994 | Weldon et al. | 604/271 |
| 5,370,660 | 12/1994 | Weinstein et al. | 606/215 |
| 5,372,585 | 12/1994 | Tiefenbrun et al. | 604/59 |

FOREIGN PATENT DOCUMENTS

| | | |
|---|---|---|
| 1162904 | 2/1984 | Canada . |
| 0138448 | 4/1985 | European Pat. Off. . |
| 0543499 | 5/1993 | European Pat. Off. . |
| 5-123329 | 5/1993 | Japan . |
| 1196049 | 6/1970 | United Kingdom . |

OTHER PUBLICATIONS

Carton, Charles A., et al., "Experimental Studies in the Surgery of Small Blood Vessels, IV. Nonsuture Anastomosis of Arteries and Veins, Using Flanged Ring Protheses and Plastic Adhesive," *Surgical Forum*, vol. 11 (1960) pp. 238–239.

Matsumoto, Teruo, "Tissue Adhesives in Surgery," pp. 226–237.

Tseng, Yin–Chao, et al., "In vitro Toxicity Test of 2-cyanoacrylate Polymers by Cell Culture Method," *J. Biomedical Materials Research*, vol. 24, 1355–1367 (1990).

"Methods of Abating Residual Formaldehyde in Indistrial Resins," EPO Applied Technology Series vol. 10.

"Synthesis and Degradation of Poly(alkyl a–Cyanoacrylate)," F. Leonard, Journal of Applied Science, vol. 10, pp. 259–272, 1966.

"The N–Alkylalphacyanoacrylate Tissue Adhesives," F. Leonard, Annals New York Academy of Sciences, vol. 146, pp. 203–213, 1968.

(List continued on next page.)

*Primary Examiner*—Carlos Azpuru
*Attorney, Agent, or Firm*—Oliff & Berridge

[57] ABSTRACT

A biocompatible monomer composition contains (A) at least one monomer of the formula:

CHR=CXY wherein X and Y are each strong electron withdrawing groups, and R is H or, provided that X and Y are both cyano groups, a $C_1$–$C_4$ alkyl group; and (B) an effective amount of at least one biocompatible agent effective to reduce active formaldehyde concentration levels, preferably a formaldehyde scavenger compound. The monomer is preferably an alpha-cyanoacrylate. The formaldehyde scavenger compound may be in microencapsulated or non-microencapsulated form. The composition can be applied to a variety of materials and is particularly suitable as in vivo tissue adhesive. A method of joining together in vivo two surfaces, e.g., body tissues, includes (a) applying to at least one of the surfaces a composition containing 1) at least one monomer, preferably an alpha-cyanoacrylate, which forms a polymer whose in vivo biodegradation produces formaldehyde; and 2) an effective amount of at least one biocompatible agent effective to reduce active formaldehyde concentration levels, preferably a formaldehyde scavenger; and (b) maintaining the surfaces in contact until the composition polymerizes.

17 Claims, No Drawings

OTHER PUBLICATIONS

"In vivo Evaluation of 2-Cyanocrylates as Surgical Adhesives," Yin-Chao Tseng, et al., Journal of Applied Biomaterials, vol. 1, pp. 111–119, 1990.

"In vitro Heterogeneous Degradation of poly (n-alkyl a-cyanoacrylate," W. R. Vezin et al., Journal of Biomedical Materials Research, vol. 14, pp. 93–106, 1980.

"Histotoxicity of Cyanoacrylate Tissue Adhesive in the Rat," S. C. Woodward et al., Annals of Surgery, vol. 162, pp. 113–122, 1965.

"Cytotoxicity of alkyl-2-cyanoacrylate Adhesives," F. J. Papatheofanis, Journal of Biomedical Materials Research, vol. 23, pp. 661–668, 1989.

"Evaluation of Formaldehyde Scavengers," C. Tomasino et al., vol. 16, No. 12, pp. 259–265, 1964.

"A Search for Potential Formaldehyde Acceptors," R. S. Perry et al., vol. 12, No. 12, pp. 311–316, 1980.

"Toxicity of the Cyanoacrylates," S. B. Aronson et al., Arch Ophthal, vol. 84, pp. 342–348, 1970.

"Carbohydrazide Found to Be An Effective Scavenger for Reducing Free Formaldehyde," R. E. Silva, Jr. et al., vol. 13, pp. 29–39, 1981.

BIOCOMPATIBLE MONOMER AND POLYMER COMPOSITIONS

This is a division of application No. 08/215,584 filed Mar. 22, 1994, now U.S. Pat. No. 5,514,371, which in turn is a division of application No. 08/040,618 filed Mar. 31, 1993, now U.S. Pat. No. 5,328,687.

BACKGROUND OF THE INVENTION

1. Field of the Invention

This invention relates to monomer and polymer compositions useful to form biomedical adhesives, sealants, bioactive agent release matrices, and implants. More particularly, this invention relates to biocompatible monomer and polymer compositions particularly useful for medical, surgical and other in vivo applications.

2. Related Developments

The products in primary use for wound closure are surgical sutures and staples. Sutures are recognized to provide adequate wound support. However, sutures cause additional trauma to the wound site (by reason of the need for the needle and suture to pass through tissue) and are time-consuming to place, and, at skin level, can cause unattractive wound closure marks. Surgical staples have been developed to speed wound apposition and provide improved cosmetic results. However, surgical staples also impose additional wound trauma and require the use of ancillary and often expensive devices for positioning and applying the staples.

To overcome these drawbacks, fast-acting surgical adhesives have been proposed. One group of such adhesives is the monomeric forms of alpha-cyanoacrylates.

Reference is made, for example, to U.S. Pat. Nos. 3,527,841 (Wicker et al.); 3,722,599 (Robertson et al.); 3,995,641 (Kronenthal et al.); and 3,940,362 (Overhults), which disclose that alpha-cyanoacrylates are useful as surgical adhesives. All of the foregoing references are hereby incorporated by reference herein.

Typically, when used as adhesives and sealants, cyanoacrylates are applied in monomeric form to the surfaces to be joined or sealed, where, typically, in situ anionic polymerization of the monomer occurs, giving rise to the desired adhesive bond or seal. Implants, such as rods, meshes, screws, and plates, may be formed of cyanoacrylate polymers, formed typically by radical-initiated polymerization.

However, a drawback to the in vivo biomedical use of alpha-cyanoacrylate monomers and polymers has been their potential for causing adverse tissue response. For example, methyl alpha-cyanoacrylate has been reported to cause tissue inflammation at the site of application.

The adverse tissue response to alpha-cyanoacrylates appears to be caused by the products released during in vivo biodegradation of the polymerized alpha-cyanoacrylates. It is believed that formaldehyde is the biodegradation product most responsible for the adverse tissue response and, specifically, the high concentration of formaldehyde produced during rapid polymer biodegradation. Reference is made, for example, to F. Leonard et al., Journal of Applied Polymer Science, Vol. 10, pp. 259–272 (1966); F. Leonard, Annals New York Academy of Sciences, Vol. 146, pp. 203–213 (1968); Tseng, Yin-Chao, et al., Journal of Applied Biomaterials, Vol. 1, pp. 111–119 (1990), and to Tseng, Yin-Chao, et al., Journal of Biomedical Materials Research, Vol. 24, pp. 1355–1367 (1990), which are both hereby incorporated by reference herein.

For these reasons, cyanoacrylates have not come into widespread use for biomedical purposes.

Efforts to increase the tissue compatibility of alpha-cyanoacrylates have included modifying the alkyl ester group. For example, increasing the alkyl ester chain length to form the higher cyanoacrylate analogues, e.g., butyl-2-cyanoacrylates and octyl-2-cyanoacrylates, has been found to improve biocompatibility but the higher analogues biodegrade at slower rates than the lower alkyl cyanoacrylates.

Other examples of modified alpha-cyanoacrylates used in biomedical applications include carbalkoxyalkyl alpha-cyanoacrylates (see, for example, U.S. Pat. No. 3,995,641 to Kronenthal et al.), fluorocyanoacrylates (see, for example, U.S. Pat. No. 3,722,599 to Robertson et al.), and alkoxyalkyl 2-cyanoacrylates (see, for example, U.S. Pat. No. 3,559,652 to Banitt et al.). Other efforts have included mixing alpha-cyanoacrylates with dimethyl methylenemalonate and higher esters of 2-cyanoacrylic acid (see, for example, U.S. Pat. No. 3,591,676 to Hawkins et al.).

In other efforts to increase the usefulness of alpha-cyanoacrylate adhesive compositions for surgical applications, certain viscosity modifiers have been used in combination with alkyl alpha-cyanoacrylate monomers, such as methyl alpha-cyanoacrylate. See, for example, U.S. Pat. Nos. 3,564,078 (wherein the viscosity modifier is poly(ethyl 2-cyanoacrylate)) and 3,527,841 (wherein the viscosity modifier is poly(lactic acid)), both patents being to Wicker et al.

Techniques for suppressing formaldehyde in industrial processes utilizing synthetic polymeric resins are known. However, the concept of suppressing formaldehyde as a mechanism for improving biocompatibility of polymers that biodegrade in vivo has not been suggested.

SUMMARY OF THE INVENTION

The present invention is based on the discovery that combining the monomers described hereinafter, and particularly the alpha-cyanoacrylate monomer(s), with a biocompatible agent effective to reduce active formaldehyde concentration levels, preferably a formaldehyde scavenger, which may be either in microencapsulated form or in non-microencapsulated form, will substantially improve the biocompatibility of polymers formed from such monomers. Furthermore, the present invention increases the biocompatibility of lower alkyl alpha-cyanoacrylate monomers and polymers and therefore increases the effectiveness of such monomers and polymers in in vivo applications.

Accordingly, one embodiment of the present invention provides a biocompatible monomer composition, comprising:

A) at least one monomer of the formula:

wherein X and Y are each strong electron withdrawing groups, and R is H, or, provided that X and Y are both cyano groups, a $C_1$–$C_4$ alkyl group; and B) an effective amount of at least one biocompatible agent effective to reduce active formaldehyde concentration levels.

In another embodiment, the present invention is directed to a biocompatible composition comprising A) at least one copolymer of two monomers of formula (I) or one monomer of formula (I) and a monomer having the formula:

wherein X and Y are as defined above and Z is —CH=CH$_2$ and component B) described above.

In a further embodiment, the present invention is directed to a biocompatible composition comprising A) a polymer whose in vivo biodegradation produces formaldehyde and component B) described above.

In other embodiments, the present invention is directed to methods of using the above-described monomers, copolymers and polymers made therefrom for biomedical purposes.

Preferably, the monomer is an alpha-cyanoacrylate. The monomer compositions of this invention and polymers formed therefrom are useful as tissue adhesives, sealants for preventing bleeding or for covering open wounds, systems for delivery of therapeutic or other bioactive agents, and in other biomedical applications. They find uses in, for example, apposing surgically incised or traumatically lacerated tissues; setting fractured bone structures; retarding blood flow from wounds; aiding repair and regrowth of living tissue; as matrices for delivering bioactive agents and as implants.

DETAILED DESCRIPTION OF PREFERRED EMBODIMENTS

The monomers of formula (I) used in this invention are polymerizable, e.g. anionically polymerizable or free radical polymerizable, to form polymers which biodegrade to form active formaldehyde. As used herein, the language "active formaldehyde" refers to formaldehyde which is active so as to cause adverse tissue response.

Examples of monomers within the scope of formula (I) include alpha-cyanoacrylates, vinylidene cyanides, $C_1$–$C_4$ alkyl homologues of vinylidene cyanides, dialkyl methylene malonates, acylacrylonitriles, vinyl sulfinates and vinyl sulfonates of the formula $CH_2$=CX'Y' wherein X' is —$SO_2R'$ or —$SO_3R'$ and Y' is —CN, —COOR', —$COCH_3$, —$SO_2R'$ or —$SO_3R'$, and R' is H or hydrocarbyl.

Preferred monomers of formula (I) for use in this invention are alpha-cyanoacrylates. These monomers are known in the art and have the formula

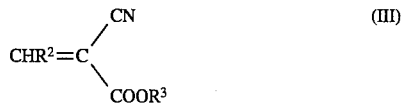

(III)

wherein $R^2$ is hydrogen and $R^3$ is a hydrocarbyl or substituted hydrocarbyl group; a group having the formula —$R^4$—O—$R^5$—O—$R^6$, wherein $R^4$ is a 1,2-alkylene group having 2–4 carbon atoms, $R^5$ is an alkylene group having 2–4 carbon atoms, and $R^6$ is an alkyl group having 1–6 carbon atoms; or a group having the formula

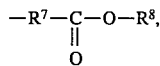

wherein $R^7$ is

or —$C(CH_3)_2$— and $R^8$ is an organic radical.

Examples of suitable hydrocarbyl and substituted hydrocarbyl groups include straight chain or branched chain alkyl groups having 1–16 carbon atoms; straight chain or branched chain $C_1$–$C_{16}$ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms; cycloalkyl groups; aralkyl groups; alkylaryl groups; and aryl groups.

The organic radical $R^8$ may be substituted or unsubstituted and may be straight chain, branched or cyclic, saturated, unsaturated or aromatic. Examples of such organic radicals include $C_1$–$C_8$ alkyl radicals, $C_2$–$C_8$ alkenyl radicals, $C_2$–$C_8$ alkynyl radicals, $C_3$–$C_{12}$ cycloaliphatic radicals, aryl radicals such as phenyl and substituted phenyl and aralkyl radicals such as benzyl, methylbenzyl and phenylethyl. Other organic radicals include substituted hydrocarbon radicals, such as halo- (e.g., chloro-, fluoro- and bromo-substituted hydrocarbons) and oxy- (e.g., alkoxy substituted hydrocarbons) substituted hydrocarbon radicals. Preferred organic radicals are alkyl, alkenyl and alkynyl radicals having from 1 to about 8 carbon atoms, and halosubstituted derivatives thereof. Particularly preferred are alkyl radicals of 4 to 6 carbon atoms.

In the cyanoacrylate monomer of formula (III), $R^3$ is preferably an alkyl group having 1–10 carbon atoms or a group having the formula —$AOR^9$, wherein A is a divalent straight or branched chain alkylene or oxyalkylene radical having 2–8 carbon atoms, and $R^9$ is a straight or branched alkyl radical having 1–8 carbon atoms.

Examples of groups represented by the formula —$AOR^9$ include 1-methoxy-2-propyl, 2-butoxy ethyl, isopropoxy ethyl, 2-methoxy ethyl, and 2-ethoxy ethyl.

The most preferred alpha-cyanoacrylate monomers used in this invention are methyl alpha-cyanoacrylate, butyl alpha-cyanoacrylate, octyl alpha-cyanoacrylate, 1-methoxy-2-propyl cyanoacrylate, 2-butoxy ethyl cyanoacrylate, and isopropoxy-ethyl cyanoacrylate.

The alpha-cyanoacrylates of formula (III) wherein $R^3$ is a hydrocarbyl or substituted hydrocarbyl group can be prepared according to methods known in the art. Reference is made, for example, to U.S. Pat. Nos. 2,721,858 and 3,254,111, each of which is hereby incorporated by reference herein. For example, the alpha cyanoacrylates can be prepared by reacting an alkyl cyanoacetate with formaldehyde in a non-aqueous organic solvent and in the presence of a basic catalyst, followed by pyrolysis of the anhydrous intermediate polymer in the presence of a polymerization inhibitor. The alpha-cyanoacrylate monomers prepared with low moisture content and essentially free of impurities are preferred for biomedical use.

The alpha-cyanoacrylates of formula (III) wherein $R^3$ is a group having the formula —$R^4$—O—$R^5$—O—$R^6$ can be prepared according to the method disclosed in U.S. Pat. No. 4,364,876 (Kimura et al.), which is hereby incorporated by reference herein. In the Kimura et al. method, the alpha-cyanoacrylates are prepared by producing a cyanoacetate by esterifying cyanoacetic acid with an alcohol or by transesterifying an alkyl cyanoacetate and an alcohol; condensing the cyanoacetate and formaldehyde or para-formaldehyde in the presence of a catalyst at a molar ratio of 0.5–1.5:1, preferably 0.8–1.2:1, to obtain a condensate; depolymerizing the condensation reaction mixture either directly or after removal of the condensation catalyst to yield crude cyanoacrylate; and distilling the crude cyanoacrylate to form a high purity cyanoacrylate.

The alpha-cyanoacrylates of formula (III) wherein $R^3$ is a group having the formula

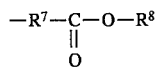

can be prepared according to the procedure described in U.S. Pat. No. 3,995,641 (Kronenthal et al.), which is hereby incorporated by reference herein. In the Kronenthal et al. method, such alpha-cyanoacrylate monomers are prepared by reacting an alkyl ester of an alpha-cyanoacrylic acid with a cyclic 1,3-diene to form a Dieis-Alder adduct which is then subjected to alkaline hydrolysis followed by acidification to form the corresponding alpha-cyanoacrylic acid adduct. The alpha-cyanoacrylic acid adduct is preferably esterified by an alkyl bromoacetate to yield the corresponding carbalkoxymethyl alpha-cyanoacrylate adduct. Alternatively, the alpha-cyanoacrylic acid adduct may be converted to the alpha-cyanoacrylyl halide adduct by reaction with thionyl chloride. The alpha-cyanoacrylyl halide adduct is then reacted with an alkyl hydroxyacetate or a methyl substituted alkyl hydroxyacetate to yield the corresponding carbalkoxymethyl alpha-cyanoacrylate adduct or carbalkoxy alkyl alpha-cyanoacrylate adduct, respectively. The cyclic 1,3-diene blocking group is finally removed and the carbalkoxy methyl alpha-cyanoacrylate adduct or the carbalkoxy alkyl alpha-cyanoacrylate adduct is converted into the corresponding carbalkoxy alkyl alpha-cyanoacrylate by heating the adduct in the presence of a slight deficit of maleic anhydride.

Examples of monomers of formula (II) include cyanopentadienoates and alpha-cyanoacrylates of the formula:

 (IV)

wherein Z is —CH=CH$_2$ and $R^3$ is as defined above. The monomers of formula (IV) wherein $R^3$ is an alkyl group of 1–10 carbon atoms, i.e., the 2-cyanopenta-2,4-dienoic acid esters, can be prepared by reacting an appropriate 2-cyanoacetate with acrolein in the presence of a catalyst such as zinc chloride. This method of preparing 2-cyanopenta-2,4-dienoic acid esters is disclosed, for example, in U.S. Pat. No. 3,554,990, which is hereby incorporated by reference herein.

Component B) of the compositions of this invention is at least one biocompatible agent effective to reduce active formaldehyde concentration levels (also referred to herein as "formaldehyde concentration reducing agents"). Preferably, component B) is a formaldehyde scavenger compound. Examples of formaldehyde scavenger compounds useful in this invention include sulfites; bisulfites; mixtures of sulfites and-bisulfites; ammonium sulfite salts; amines; amides; imides; nitriles; carbamates; alcohols; mercaptans; proteins; mixtures of amines, amides, and proteins; active methylene compounds such as cyclic ketones and compounds having a β-dicarbonyl group; and heterocyclic ring compounds free of a carbonyl group and containing an NH group, with the ring made up of nitrogen or carbon atoms, the ring being unsaturated or, when fused to a phenyl group, being unsaturated or saturated, and the NH group being bonded to a carbon or a nitrogen atom, which atom is directly bonded by a double bond to another carbon or nitrogen atom.

Bisulfites and sulfites useful as the formaldehyde scavenger compound in this invention include alkali metal salts such as lithium, sodium and potassium salts, and ammonium salts, for example, sodium bisulfite, potassium bisulfite, lithium bisulfite, ammonium bisulfite, sodium sulfite, potassium sulfite, lithium sulfite, ammonium sulfite, and the like.

Examples of amines useful in this invention include the aliphatic and aromatic amines such as, for example, aniline, benzidine, aminopyrimidine, toluene-diamine, triethylenediamine, diphenylamine, diaminodiphenylamine, hydrazines and hydrazide.

Suitable proteins include collagen, gelatin, casein, soyabean protein, vegetable protein, keratin and glue. The preferred protein for use in this invention is casein.

Suitable amides for use in this invention include urea, cyanamide, acrylamide, benzamide, and acetamide. Urea is the preferred amide.

Suitable alcohols include phenols, 1,4-butanediol, d-sorbitol, and polyvinyl alcohol.

Examples of suitable compounds having a β-dicarbonyl group include malonic acid, acetylacetone, ethylacetone, acetate, malonamide, diethylmalonate or another malonic ester.

Preferred cyclic ketones for use in this invention include cyclohexanone or cyclopentanone.

Examples of suitable heterocyclic compounds for use as the formaldehyde scavenger in this invention are disclosed, for example, in U.S. Pat. No. 4,127,382 (Perry) which is hereby incorporated by reference herein. Such heterocyclic compounds include, for example, benzimidazole, 5-methyl benzimidazole, 2-methylbenzimidazole, indole, pyrrole, 1,2, 4-triazole, indoline, benzotriazole, indoline, and the like.

The preferred formaldehyde scavenger for use in this invention is sodium bisulfite.

In practicing this invention, the formaldehyde concentration reducing agent, e.g., formaldehyde scavenger compound, is added in an effective amount to the cyanoacrylate. The "effective amount" is that amount sufficient to reduce the amount of formaldehyde generated during subsequent in vivo biodegradation of the polymerized cyanoacrylate. This amount will depend on the type of active formaldehyde concentration reducing agent, and can be readily determined without undue experimentation by those skilled in the art.

The formaldehyde concentration reducing agent may be used in this invention in either free form or in microencapsulated form.

When microencapsulated, the formaldehyde concentration reducing agent is released from the microcapsule continuously over a period of time during the in vivo biodegradation of the cyanoacrylate polymer.

For purposes of this invention, the microencapsulated form of the formaldehyde concentration reducing agent is preferred because this embodiment prevents or substantially reduces polymerization of the cyanoacrylate monomer by the formaldehyde concentration reducing agent, which increases shelf-life and facilitates handling of the monomer composition during use.

Microencapsulation of the formaldehyde scavenger can be achieved, by many known microencapsulation techniques. For example, microencapsulation can be carried out by dissolving a coating polymer in a volatile solvent, e.g., methylene chloride, to a polymer concentration of about 6% by weight; adding a formaldehyde scavenger compound in particulate form to the coating polymer/solvent solution under agitation to yield a scavenger concentration of 18% by weight; slowly adding a surfactant-containing mineral oil solution to the polymer solution under rapid agitation; allowing the volatile solvent to evaporate under agitation; removing the agitator; separating the solids from the mineral oil; and washing and drying the microparticles. The size of the microparticles will range from about 0.001 to about 1000 microns.

The coating polymer for microencapsulating the formaldehyde concentration reducing agent should be polymers which undergo in vivo bioerosion, preferably at rates similar to or greater than the cyanoacrylate polymer formed by the monomer, and should have low inherent moisture content. Such "bioerosion" can occur as a result of the physical or chemical breakdown of the encapsulating material, for example, by the encapsulating material passing from solid to solute in the presence of body fluids, or by biodegradation of the encapsulating material by agents present in the body.

Examples of coating materials which can be used to microencapsulate the formaldehyde concentration reducing agent include polyesters, such as polyglycolic acid, polylactic acid, copolymers of polyglycolic acid and polylactic acid, polycaprolactone, poly-β-hydroxybutyrate, copolymers of epsilon-caprolactone and delta-valerolactone, copolymers of epsilon-caprolactone and DL-dilactide, and polyester hydrogels; polyvinylpyrrolidone; polyamides; gelatin; albumin; proteins; collagen; poly(orthoesters); poly(anhydrides); poly(alkyl-2-cyanoacrylates); poly(dihydropyrans); poly(acetals); poly(phosphazenes); poly(urethanes); poly(dioxinones); cellulose; and starches.

Examples of the surfactant which can be added to the mineral oil include those commercially available under the designations Triton x-100, Tween 20 and Tween 80.

The composition of this invention may further contain a stabilizer and/or one or more adjuvant substances, such as thickening agents, plasticizers, or the like, to improve the medical utility of the monomer for particular medical applications.

Examples of suitable stabilizers include sulfur dioxide, sulfonic acid, lactone, boron trifluoride, hydroquinone, hydroquinone monomethyl ether, catechol, pyrogallol, benzoquinone, 2-hydroxybenzoquinone, p-methoxy phenol, t-butyl catechol, organic acid, butylated hydroxy anisole, butylated hydroxy toluene, t-butyl hydroquinone, alkyl sulfate, alkyl sulfite, 3-sulfolene, alkylsulfone, alkyl sulfoxide, mercaptan, and alkyl sulfide.

Suitable thickeners include, for example, polycyanoacrylates, polylactic acid, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene.

Examples of suitable plasticizers include dioctyl phthalate, dimethyl sebacate, triethyl phosphate, tri(2-ethylhexyl)phosphate, tri(p-cresyl) phosphate, glyceryl triacetate, glyceryl tributyrate, diethyl sebacate, dioctyl adipate, isopropyl myristate, butyl stearate, lauric acid, dibutyl phthalate, trioctyl trimellitate, and dioctyl glutarate.

To improve the cohesive strength of adhesives formed from the compositions of this invention, difunctional monomeric cross-linking agents may be added to the monomer compositions of this invention. Such crosslinking agents are known. Reference is made, for example, to U.S. Pat. No. 3,940,362 (Overhults), which is hereby incorporated by reference herein. Examples of suitable crosslinking agents include alkyl bis(2-cyanoacrylates), triallyl isocyanurates, alkylene diacrylates, alkylene dimethacrylates, trimethylol propane triacrylate, and alkyl bis(2-cyanoacrylates). A catalytic amount of a free radical initiator is added to initiate polymerization of the cyanoacrylate monomer/crosslinking agent blend. Such compositions can be molded or otherwise formed to provide preformed implants for surgical use, such as rods, meshes, plates, and screws.

The compositions of this invention may further contain fibrous reinforcement and colorants, i.e., dyes and pigments. Examples of suitable fibrous reinforcement include PGA microfibrils, collagen microfibrils, cellulosic microfibrils, and olefinic microfibrils. Examples of suitable colorants include 1-hydroxy-4-[4-methylphenylamino]-9,10 anthracenedione (D+C violet No. 2); disodium salt of 6-hydroxy-5-[(4-sulfophenyl)axo]-2-naphthalenesulfonic acid (FD+C Yellow No. 6); 9-(o-carboxyphenyl)-6-hydroxy-2,4,5,7-tetraiodo-3H-xanthen-3-one, disodium salt, monohydrate (FD+C Red No. 3); 2-(1,3-dihydro-3-oxo-5-sulfo-2H-indol-2-ylidene)-2,3-dihydro-3-oxo-1H-indole-5 -sulfonic acid disodium salt (FD+C Blue No. 2); and [phthalocyaninato (2-)] copper.

The compositions of this invention can be used to join together two surfaces by applying the particular composition to at least one of said surfaces. Depending on the particular requirements of the user, the adhesive compositions of this invention can be applied by known means such as with a glass stirring rod, sterile brush or medicine dropper; however, in many situations a pressurized aerosol dispensing package is preferred in which the adhesive composition is in solution with a compatible anhydrous propellant. Aerosol application of the monomers is particularly advantageous for use in hemostasis.

In one embodiment, the present invention is directed to a method of joining together in vivo two surfaces which comprises (a) applying to at least one of said surfaces a composition of this invention, e.g., a composition comprising 1) at least one monomer (e.g., a monomer of formula (I)) which forms a polymer whose in vivo biodegradation produces formaldehyde; and 2) an effective amount of a biocompatible agent effective to reduce active formaldehyde concentration levels, preferably a formaldehyde scavenger compound; and (b) maintaining the surfaces in contact until said composition polymerizes. One of said surfaces can be body tissue and the other surface a prosthetic device, or both surfaces may be body tissue.

In another embodiment, the present invention is directed to a method for effecting in vivo administration of a bioactive agent, comprising introducing into a body a composition comprising a polymer whose in vivo biodegradation produces formaldehyde, an effective amount of at least one biocompatible agent effective to reduce active formaldehyde concentration levels, and a bioactive amount of a bioactive agent, wherein biodegradation of the polymer effects in vivo release of the bioactive agent. The bioactive agent may be encapsulated in a suitable biogradable material for controlling release of the bioactive agent.

Specific methods which may use a composition containing a monomer, the polymeric form of which produces formaldehyde upon in vivo biodegradation and an effective amount of a biocompatible agent effective to reduce active formaldehyde concentration levels, preferably a formaldehyde scavenger compound, include methods for repairing damaged living tissue to prevent the escape of fluids therethrough which comprises (a) applying to the tissue said monomer/formaldehyde concentration reducing agent composition; and (b) allowing the composition to polymerize; methods for stemming the flow of blood from small vessels which comprises applying to said vessels a hemostatic agent comprising the monomer/formaldehyde concentration reducing agent composition; methods of dressing burns to promote the healing thereof which comprises (a) covering said burn with the monomer/formaldehyde concentration reducing agent composition; and (b) allowing the composition to polymerize; and methods of dressing wounds to promote the healing thereof which comprises (a) covering said wound with the monomer/formaldehyde concentration reducing agent composition; and (b) allowing the composition to polymerize.

Repairing injured tissues (for example, to control bleeding) comprises, in general, sponging to remove superficial body fluids and subsequent application to the exposed tissue of an adhesive composition containing a cyanoacrylate monomer. The composition polymerizes to a thin film of polymer while in contact with the tissue surface. Tissues which are not bleeding or otherwise covered by body fluids need not be sponged first. For bonding separate surfaces of body tissues, the monomer is applied to at least one surface, and the surfaces are brought quickly together while the monomer polymerizes in contact with both of the surfaces.

The compositions may further be used to administer therapeutic agents into the body. The composition will form a matrix for the therapeutic agent, with the therapeutic agent being released in vivo over time from the matrix during biodegradation of the polymer. Specifically, a composition comprising the monomer (or polymer form of the monomer, since in this particular application, polymerization need not occur in situ), a biocompatible agent effective to reduce active formaldehyde concentration levels, preferably a formaldehyde scavenger compound, and a therapeutic agent is introduced into the body where the polymer undergoes biodegradation, releasing the therapeutic agent.

The monomers are readily polymerized to addition type polymers and copolymers, which are generally optically clear (as films).

In most bonding applications using the compositions of this invention, polymerization of the monomers is catalyzed by small amounts of moisture on the surface of the adherents; thus desired bonding of tissues or hemostasis proceeds well in the presence of blood and other body fluids. The bonds formed are of adequate flexibility and strength to withstand normal movement of tissue. In addition, bond strength is maintained as natural wound healing proceeds concurrently with polymer assimilation.

Compositions employed in the invention are sterilizable by conventional methods such as by autoclave or by aseptic filtration techniques.

The invention is further illustrated by the following non-limiting examples.

EXAMPLES

In the Examples below, the following terms are defined as follows:
MCA—methyl cyanoacrylate
IPECA—isopropoxyethyl cyanoacrylate
2-BECA—2-butoxy ethyl cyanoacrylate
MPCA—1-methoxy-2-propyl cyanoacrylate
monomer(s)—refers generically to MCA, IPECA, 2-BECA, and/or MPCA Examples 1–12 and Control Examples A–C Examples 1–12 and Control Examples A–C illustrate the effect of a formaldehyde scavenger on the amount of formaldehyde released during the biodegradation of a cyanoacrylate polymer. The compositions of Examples 1–12 each contain a formaldehyde scavenger while the compositions of Control Examples A–C do not.

The formulations of the compositions prepared in Examples 1–12 and Control Examples A–C are shown in Table I below.

The compositions of the examples are prepared as follows. The monomer and formaldehyde scavenger, in the appropriate weight ratio, are mixed thoroughly by shaking. (Solid formaldehyde scavengers are ground or milled to a fine particle size prior to mixing.) The resulting mixture is quickly poured over an aluminum mesh (½"×5" approximately) which is resting on a Teflon® sheet. The mesh is wetted to the fullest extent but not overflowed. Polymerization of the cyanoacrylate mixture is then accelerated by spraying with a 1% aqueous sodium bicarbonate solution. The hardened polymer supported by the aluminum mesh is gently scraped off from the Teflon(R) sheet, rinsed with water and dried.

In vitro biodegradation of the polymer films is then carried out as follows. The mesh-supported polymer film is placed in a PH 7.41 buffer solution (monobasic potassium phosphate and disodium phosphate). Biodegradation is carried out at 80°±2° C. for 75 hours. The partially degraded film is separated from the buffer solution, rinsed with water and dried. The buffer solution is centrifuged, and the clear solution thus obtained is then subjected to formaldehyde determination.

The amount of formaldehyde generated during biodegradation of the polymer films is determined by means of a spectrophotometric method using Nash's Reagent. This method is similar to Method 964.21 described in AOAC Official Methods of Analysis, 1990, Volume 2, p. 1037. In the following tables, the term "ug formaldehyde/mg polymer" means the amount of formaldehyde generated in micrograms divided by the original polymer weight in milligrams (excluding the weight of the scavenger).

The results are presented in Table I.

TABLE I

Examples 1–12 and Control Examples A–C:
Formulations and Formaldehyde Generation

| Example No. | Monomer | Formaldehyde Scavenger | Scavenger Weight % | μg Formaldehyde Detected Per mg Polymer | % Reduction of Formaldehyde Detected |
|---|---|---|---|---|---|
| 1 | MCA | 1,4 butandediol | 20 | 1.25 | —* |
| 2 | MCA | diphenylamine | 20 | 0.53 | 51 |
| 3 | MCA | gelatin | 20 | 1.04 | 5 |
| 4 | MCA | casein | 20 | 1.36 | —* |
| A | MCA | None-Control for Ex. 1–4 | 0 | 1.09 | 0 |
| 5 | IPECA | sodium bisulfite | 20 | <0.05 | 100 |
| 6 | IPECA | urea | 20 | 0.12 | 88 |
| 7 | IPECA | casein | 30 | 0.08 | 92 |
| 8 | IPECA | polyvinyl alcohol | 30 | 0.22 | 79 |
| B | IPECA | None-Control for Ex. 5–8 | 0 | 1.03 | 0 |
| 9 | IPECA | acrylamide | 20 | 0.18 | 70 |

TABLE I-continued

Examples 1–12 and Control Examples A–C:
Formulations and Formaldehyde Generation

| Example No. | Monomer | Formaldehyde Scavenger | Scavenger Weight % | µg Formaldehyde Detected Per mg Polymer | % Reduction of Formaldehyde Detected |
|---|---|---|---|---|---|
| 10 | IPECA | D-sorbitol | 20 | 0.25 | 58 |
| 11 | IPECA | 4-methoxyphenol | 20 | 0.44 | 27 |
| 12 | IPECA | 1,3-dihydroxy-2-propanone | 20 | 0.44 | 27 |
| C | IPECA | None-Control for Ex. 9–12 | 0 | 0.60 | 0 |

*No reduction detected. The reason that the amount of formaldehyde detected in these samples is greater than the control is believed to result from the fact that the MCA/scavenger composition degraded faster than the control, with a 75–95% weight loss of the MCA/scavenger compositions compared with approximately a 50% weight loss of the control.

The results set forth in Table I show that a significant reduction of formaldehyde generation occurs during polymer biodegradation when a formaldehyde scavenger is present.

Examples 13–20 and Control Examples D–G

Examples 13–20 and Control Examples D–G illustrate the effect of a microencapsulated formaldehyde scavenger on the amount of formaldehyde generated during cyanoacrylate polymer biodegradation. The compositions of Examples 13–20 contain microencapsulated formaldehyde scavengers while the compositions of the Control Examples do not contain any formaldehyde scavenger.

The formulations of the compositions prepared in Examples 13–20 and Control Examples D–G are shown in Table II below.

The compositions of these examples are prepared in the same manner as are the compositions in Examples 1–12 and Control Examples A–C, except that the formaldehyde scavenger is used in microencapsulated form. Microencapsulation of the scavenger is carried out as follows. In a 500 ml resin kettle, a coating polymer (e.g., polyglycolic-colactic acid, polyvinylpyrrolidone, or polycaprolactone) is dissolved in a volatile solvent, e.g., methylene chloride. The final concentration is approximately 6% (w/v). The particulate scavenger (e.g., sodium bisulfite, urea, casein, or polyvinyl alcohol) is then added to the solution under agitation. Its concentration with respect to the solution volume is approximately 18%. In a separate container, a 1% surfactant (e.g., Triton x-100, Tween 20, or Tween 80) in mineral oil is prepared. Under rapid agitation, the mineral oil solution is slowly added to the polymer solution. The volatile solvent is allowed to evaporate under agitation. This typically is allowed to proceed for 12–20 hours under ambient conditions. At the end of this period, the agitator is removed and the solids are separated from the mineral oil. The particles are washed in hexane 3–4 times and dried. The resulting particles range in size from 10–1000 microns.

In vitro degradation of the polymer films and formaldehyde determination are carried out using the same procedures followed in Examples 1–12 and Control Examples A–C. The results are shown in Table II.

TABLE II

Examples 13–20 and Control Examples D–G:
Formulations and Formaldehyde Generation

| Example No. | Monomer | Microcapsule Coating/Scavenger | Microcapsule Weight % | µg Formaldehyde Detected Per mg Polymer | % Reduction of Formaldehyde Detected |
|---|---|---|---|---|---|
| 13 | MCA | 50:50 PGA/PLA/Casein | 20 | 2.0 | 57 |
| 14 | MPCA | 50:50 PGA/PLA/Sodium Bisulfite | 20 | 0.2 | 97 |
| 15 | MPCA | Polyvinyl Pyrrolidone/Urea | 20 | 0.9 | 84 |
| 16 | MPCA | 50:50 PGA/PLA/Casein | 20 | 2.2 | 62 |
| 17 | 2-BECA | 50:50 PGA/PLA/Sodium Bisulfite | 20 | <0.1 | 100 |
| 18 | 2-BECA | Polyvinyl Pyrrolidone/Urea | 20 | 1.4 | 67 |
| 19 | IPECA | Polycaprolactone/Polyvinyl Alcohol | 20 | 2.5 | 26 |
| 20 | IPECA | Polyvinyl Pyrrolidone/Urea | 20 | 1.1 | 68 |
| D | MCA | None | 0 | 4.7 | 0 |
| E | MPCA | None | 0 | 5.8 | 0 |
| F | 2-BECA | None | 0 | 4.2 | 0 |
| G | IPECA | None | 0 | 3.4 | 0 |

The results presented in Table II show that much less formaldehyde is generated during cyanoacrylate polymer degradation when a microencapsulated formaldehyde scavenger is present than when it is absent.

What is claimed is:

1. A method of dressing living tissue, comprising (a) applying to said living tissue a composition comprising 1) at least one monomer which forms a polymer whose in vivo biodegradation produces formaldehyde; and 2) an effective amount of at least one biocompatible agent effective to reduce active formaldehyde concentration levels; and (b) allowing the composition to polymerize, wherein the at least one monomer has the formula:

CHR=CXY wherein R is H, $C_1$–$C_4$ alkyl group, or —CH=$CH_2$ group, and X and Y are both strong electron withdrawing groups.

2. A method of dressing living tissue, comprising (a) applying to said living tissue a composition comprising 1) at least one monomer which forms a polymer whose in vivo biodegradation produces formaldehyde; and 2) an effective amount of at least one formaldehyde scavenger compound; and (b) allowing the composition to polymerize, wherein the at least one monomer has the formula:

CHR=CXY wherein R is H, $C_1$–$C_4$ alkyl group, or —CH=$CH_2$ group, and X and Y are both strong electron withdrawing groups.

3. A method according to claim 1, wherein the at least one monomer is an alpha-cyanoacrylate, a vinylidene cyanide, a $C_1$–$C_4$ alkyl homolog of a vinylidene cyanide, a dialkyl methylene malonate, an acylacrylonitrile, a vinyl sulfinate or vinyl sulfonate of the formula $CH_2$=CX'Y' where X' is —$SO_2R'$ or —$SO_3R'$ and Y' is —CN, —COOR, —$COCH_3$, —$SO_2R'$ or —$SO_3R'$ and R' is H or hydrocarbyl.

4. A method according to claim 3, wherein the at least one monomer is an alpha-cyanoacrylate.

5. A method according to claim 4, wherein the alpha-cyanoacrylate monomer has the formula

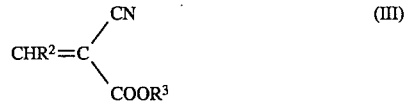

(III)

wherein $R^2$ is hydrogen and $R^3$ is a hydrocarbyl or substituted hydrocarbyl group; a group having the formula —$R^4$—O—$R^5$—O—$R^6$ wherein $R^4$ is a 1,2-alkylene group having 2–4 carbon atoms, $R^5$ is an alkylene group having 2–4 carbon atoms, and $R^6$ is an alkyl group, having 1–6 carbon atoms; or a group having the formula

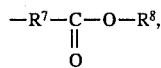

wherein $R^7$ is —$CH_2$—,

or —$C(CH_3)_2$— and $R^8$ is an organic radical.

6. A method according to claim 5, wherein $R^3$ is a hydrocarbyl or substituted hydrocarbyl group, selected from the group consisting of straight chain or branched chain alkyl groups having 1–16 carbon atoms; straight chain or branched chain $C_{1-16}$ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms; cycloalkyl groups; aralkyl groups; alkylaryl groups; and aryl groups.

7. A method according to claim 6, wherein $R^3$ is an alkyl group having 1–6 carbon atoms or a group having the formula —$AOR^9$ wherein A is a divalent straight or branched chain alkylene or oxyalkylene radical having 2–8 carbon atoms, and $R^9$ is a straight or branched alkyl radical having 1–8 carbon atoms.

8. A method according to claim 7, wherein the alpha-cyanoacrylate is methyl cyanoacrylate, butyl cyanoacrylate, octyl cyanoacrylate, 1-methoxy-2-propyl cyanoacrylate, 2-butoxy ethyl cyanoacrylate, or isopropoxy-ethyl cyanoacrylate.

9. A method according to claim 1, wherein the at least one biocompatible agent is sodium bisulfite.

10. A method according to claim 1, wherein the at least one biocompatible agent effective to reduce active formaldehyde concentration levels is in microencapsulated form.

11. A method according to claim 1, wherein the at least one biocompatible agent effective to reduce active formaldehyde concentration levels is microencapsulated with a coating polymer which undergoes in vivo bioerosion and which has a low inherent moisture content.

12. A method according to claim 11, wherein the at least one biocompatible agent effective to reduce active formaldehyde concentration levels is microencapsulated with a coating material selected from the group consisting of polyglycolic acid, polylactic acid, copolymers of polyglycolic acid and polylactic acid, polycaprolactone, poly-β-hydroxybutyrate, copolymers of epsilon-caprolactone and delta-valerolactone, copolymers of epsilon-caprolactone and DL-dilactide, polyester hydrogels, polyvinylpyrrolidone, polyamides, gelatin, albumin, proteins, collagen, poly-(orthoesters), poly(anhydrides) poly (alkyl-2-cyanoacrylates), poly(dihydropyrans), poly(acetals), poly(phosphazenes), poly(urethanes), poly(dioxinones), cellulose, and starches.

13. A method according to claim 1, wherein said living tissue comprises small blood vessels, and said method stems flow of blood from said small blood vessels by applying to said vessels a hemostatic agent comprising said composition.

14. A method according to claim 1, wherein said living tissue has been burned.

15. A method according to claim 1, wherein said living tissue is exposed in a wound.

16. A method according to claim 1, wherein the at least one monomer has the formula:

CHR=CXY wherein X and Y are each strong electron withdrawing groups, and R is H or, provided that X and Y are both cyano groups, a $C_1$–$C_4$ alkyl group.

17. A method according to claim 5, wherein $R^8$ is selected from the group consisting of straight chain or branched chain alkyl groups having 1 to 8 carbon atoms; straight chain or branched chain $C_{1-8}$ alkyl groups substituted with a halo group or an oxy group; straight chain or branched chain alkenyl groups having 2 to 8 carbon atoms; straight chain or branched chain $C_{2-8}$ alkenyl groups substituted with a halo group or an oxy group; straight chain or branched chain alkynyl groups having 2 to 8 carbon atoms; straight chain or branched chain $C_{2-8}$ alkynyl groups substituted with a halo group or an oxy group; cycloaliphatic groups having 3 to 12 carbon atoms; $C_{3-12}$ cycloaliphatic groups substituted with a halo group or an oxy group; aryl groups; aryl groups substituted with a halo group or an oxy group; aralkyl groups; and aralkyl groups substituted with a halo group or an oxy group.

* * * * *